United States Patent [19]
Elkind et al.

[11] Patent Number: 5,965,897
[45] Date of Patent: Oct. 12, 1999

[54] HIGH RESOLUTION STORAGE PHOSPHOR X-RAY IMAGING DEVICE

[75] Inventors: Valentin Elkind, Natzrat Illit; Alexander Gurevich, Ramat Gan; Michael Kogan; Boris Volfson, both of Haifa, all of Israel

[73] Assignee: X-Medica Ltd., Migdal Haemek, Israel

[21] Appl. No.: 09/018,964

[22] Filed: Feb. 5, 1998

[51] Int. Cl.$^6$ .................................................. G01N 23/04
[52] U.S. Cl. ...................... 250/585; 250/484.2; 250/581; 250/586
[58] Field of Search .............................. 378/98.8, 19, 62; 250/370.09, 584, 370.14, 370.11, 581, 585, 586, 484.2

[56] References Cited

U.S. PATENT DOCUMENTS

| | | | |
|---|---|---|---|
| 4,055,765 | 10/1977 | Gerber et al. | 250/370 |
| 4,922,103 | 5/1990 | Kawajiri et al. | 250/327.2 |
| 5,221,843 | 6/1993 | Alvarez | 250/327.2 |
| 5,654,556 | 8/1997 | Yasuda | 250/584 |

*Primary Examiner*—David P. Porta
*Assistant Examiner*—Michael J. Schwartz
*Attorney, Agent, or Firm*—Mark M. Friedman

[57] ABSTRACT

A high resolution x-ray imaging device based on a storage phosphor layer. The storage phosphor layer is sandwiched between two arrays of electrodes. In one embodiment of the device, the arrays are orthogonal arrays of linear electrodes, one of the arrays being transparent to the phosphorescence emitted by the storage phosphor. To read a pixel of a latent image stored in the storage phosphor layer, a voltage difference is established between two crossed electrodes that exceeds the threshold voltage of the storage phosphor material. The emitted light is detected by a device such as a CCD array that has coarser resolution than the crossed electrode array: the resolution of the imaging device of the present invention is the electrode width. Preferably, the electrodes are addressed for activation by optical scanning of photoconductive strips adjacent and perpendicular to the electrodes. Also preferably, the electrodes are addressed in interleaved subsets, each with as many electrode intersections as there are pixels in the CCD array, to create subimages which are interleaved to provide a final image having a resolution finer than the resolution of the CCD array. In another embodiment of the device, one array is a single electrode and the other array includes several electrodes. A subimage of the latent image is read by establishing a voltage difference between the single electrode and one of the several electrodes that exceeds the threshold voltage. The emitted light is detected by a CCD array with the resolution of the CCD array. The several subimages are assembled to provide a final image having a resolution finer than the resolution of the CCD array.

33 Claims, 7 Drawing Sheets

HIGH RESOLUTION STORAGE PHOSPHOR X-RAY IMAGING DEVICE

FIELD AND BACKGROUND OF THE INVENTION

The present invention relates to x-ray imaging devices and, more particularly, to a device for producing digital x-ray images at high resolution.

A storage phosphor is a material, such as ZnSi:Cu or $CaSO_4$:Mn, which, when locally excited by high energy photons, enters a locally excited state which is stable indefinitely. The storage phosphor can be stimulated to return to its ground state, with the accompanying emission of phosphorescent light, by stimulation, for example by intense light of a wavelength different from that of the phosphorescence, or by imposing a voltage across the storage phosphor in excess of a certain threshold that depends on the thickness and composition of the storage phosphor. The intensity of the phosphorescence is proportional to the number of photons which originally were absorbed locally by the storage phosphor to put the storage phosphor into its excited state.

Storage phosphor layers have long been used to record latent x-ray images. The intensity of the phosphorescence of the storage phosphor layer is proportional to the intensity of the x-rays to which the layer was exposed to create the latent image. Typically, a storage phosphor layer is stimulated to phosphoresce by optical scanning. Representative patents in the field include U.S. Pat. No. 4,320,296 to Ishida et al., U.S. Pat. No. 4,816,679 to Sunigawa et al., U.S. Pat. No. 4,847,498 to Saito et al., U.S. Pat. No. 4,953,038 to Schiebel et al., U.S. Pat. No. 5,376,806 to Hejazi, and U.S. Pat. No. 5,654,556 to Yasuda.

To create a digital record of the x-ray image, the light emitted by the storage phosphor layer must be converted to an electronic signal. This conversion can be performed using a charge coupled device array (CCD). In the context of such arrays, the terms "detector" and "detector element" are used interchangeably herein to denote one element of such an array. These elements also are commonly called "pixels", but to avoid confusion, the term "pixel" is used herein only for elements of images. Although CCD arrays as large as about 9000×7000 elements are available, arrays larger than about 1000×1000 are very costly and require complicated electronics and sophisticated programming techniques for real-time imaging. The smaller, less costly arrays have too few detector elements to acquire images with enough pixels for medical imaging applications such as mammography.

There is thus a widely recognized need for, and it would be highly advantageous to have, a storage-phosphor-and CCD-based x-ray imaging device that records the x-ray image at a resolution higher than the resolution of the CCD array. Such a device would enable the recording of high resolution x-ray images using relatively small and inexpensive CCD arrays.

SUMMARY OF THE INVENTION

According to the present invention there is provided an imaging system including: (a) a storage phosphor layer having two parallel planar faces; (b) a first plurality of parallel linear electrodes on a first of the two faces of the storage phosphor layer; and (c) a second plurality of parallel linear electrodes on a second of the two faces of the storage phosphor layer, the electrodes of the second plurality being oriented at an angle to the electrodes of the first plurality.

According to the present invention there is provided a method for acquiring a high-resolution x-ray image, including the steps of: (a) providing an imaging system including: (i) a storage phosphor layer having two parallel planar faces, (ii) a first plurality of parallel linear electrodes on a first of the two faces of the storage phosphor layer, and (iii) a second plurality of parallel linear electrodes of the second plurality being oriented at an angle to the electrodes of the first plurality; (b) exposing the storage phosphor layer to the x-rays, thereby creating a latent image in the storage phosphor layer; and (c) for each electrode of the first plurality and each electrode of the second plurality: applying a voltage difference, between the each electrode of the first plurality and the each electrode of the second plurality, sufficient to stimulate emission of light from a portion of the storage phosphor layer between the each electrode of the first plurality and the each electrode of the second plurality.

According to the present invention there is provided an imaging system including: (a) a storage phosphor layer; (b) an stimulation mechanism operative to stimulate emission of light from only a portion of the storage phosphor layer; and (c) an imaging mechanism operative to detect all of the light substantially simultaneously as an image including a plurality of pixels.

According to the present invention there is provided a method for acquiring a high-resolution x-ray image, including the steps of: (a) providing a storage phosphor layer; (b) exposing the storage phosphor layer to the x-rays, thereby creating a latent image in the storage phosphor layer; (c) stimulating emission of light from only a portion of the storage phosphor layer; and (d) imaging the emitted light substantially simultaneously as a plurality of pixels, thereby creating a subimage of the latent image.

The fundamental idea of the present invention is to expose a storage phosphor layer to x-rays, thereby recording a latent image, and then to stimulate, successively, only as large a portion of the storage phosphor layer as can be imaged at one time with adequate resolution by a small CCD array. Each portion may be contiguous, meaning that the portion occupies a single, well-defined area of the storage phosphor layer. Alternatively, each portion may be distributed among several subportions across the storage phosphor layer. Each time a portion is stimulated, a corresponding subimage, including at most as many pixels as there are detector elements in the CCD array, is recorded. Finally, the subimages are assembled to provide a final, high-resolution image that includes many more pixels than there are detector elements in the CCD array.

A basic device of the present invention for recording distributed subimages is a storage phosphor layer with two arrays of parallel linear electrodes, one array on either side of the storage phosphor layer. The electrodes of one array are disposed at an angle to, and preferably perpendicularly to, the electrodes of the other array. One electrode array is substantially transparent to x-rays. The other electrode array is transparent to light emitted by the storage phosphor. Applying a voltage difference greater than the threshold voltage across one electrode of the first array and one electrode of the second array causes the storage phosphor at the intersection of the two electrodes to emit light with an intensity proportional to the latent image. If the remaining electrodes are kept at a voltage relative to these two electrodes such that the voltage difference between either of these two electrodes and the remaining electrodes is less than the threshold voltage, light is emitted only at the intersection of these two electrodes. Preferably, though, this stimulation of light emission is multiplexed. Every n-th electrode of the first array and every m-th electrode of the second array is chosen to constitute a subset of the electrodes that define, at their intersections, a portion of the storage phosphor layer distributed among subportions, one subportion per intersection. For example, the odd-numbered electrodes of the first array and the odd-numbered electrodes of the second array may be chosen to constitute an electrode subset that defines a first distributed portion of the storage phosphor layer; the odd-numbered electrodes of the first array and the even-numbered electrodes of the second array may be chosen to constitute an electrode subset that defines a second distributed portion of the storage phosphor layer, etc. Applying a voltage difference in excess of the threshold across one electrode subset stimulates simultaneous emission of light from all the subportions of the corresponding portion of the storage phosphor layer. Meanwhile, the electrodes that are not members of the subset are kept at a voltage such that the voltage differences between them and the electrodes that are members of the subset is less than the threshold voltage. The light emitted from the subportions is projected optically onto a CCD array that has enough detectors for light from each stimulated subportion to impinge on one and only one detector, thereby creating a subimage in which each pixel corresponds to one stimulated subportion. This is done successively for each electrode subset. (Note that each electrode appears in more than one subset.) Finally, the subimages are interleaved to produce the final high-resolution image.

Note that the intersection regions of the various electrode subsets are themselves arranged in an interleaved manner, in exactly the same manner as the subimages are interleaved to produce the final high-resolution image. Neighboring intersection regions, each from a different electrode subset, define groups of intersection regions, such that light from each the subportions of the storage phosphor layer associated with that group is directed at one and only one of the CCD detector elements.

In an alternative embodiment, a single detector, such as a photomultiplier, is used to collect light from all the electrode intersections addressed sequentially. In this embodiment, each subimage is a single pixel of the final high-resolution image, and the final image is assembled pixel by pixel.

A basic device of the present invention for recording contiguous subimages is a storage phosphor layer with, on one side, a single electrode, and, on the other side, an array of electrodes, one electrode per contiguous portion of the storage phosphor layer. The single electrode is substantially transparent to x-rays and the electrode array is transparent to visible light, or vice versa. A voltage difference higher than the threshold voltage is established sequentially between the single electrode and each electrode of the array, stimulating emission of light from the contiguous portion of the storage phosphor layer between the single electrode and that array electrode. This light is focused on a CCD array to produce a subimage having the resolution of the CCD array. Finally, the subimages are mosaiced to produce the final high-resolution image.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of an x-ray imaging device which can be used to acquire digital x-ray images. Specifically, the present invention can be used to acquire high resolution x-ray images in conjunction with a detector, such as a CCD array, of relatively coarse resolution.

The principles and operation of an x-ray imaging device according to the present invention may be better understood with reference to the drawings and the accompanying description.

Figure 1A:
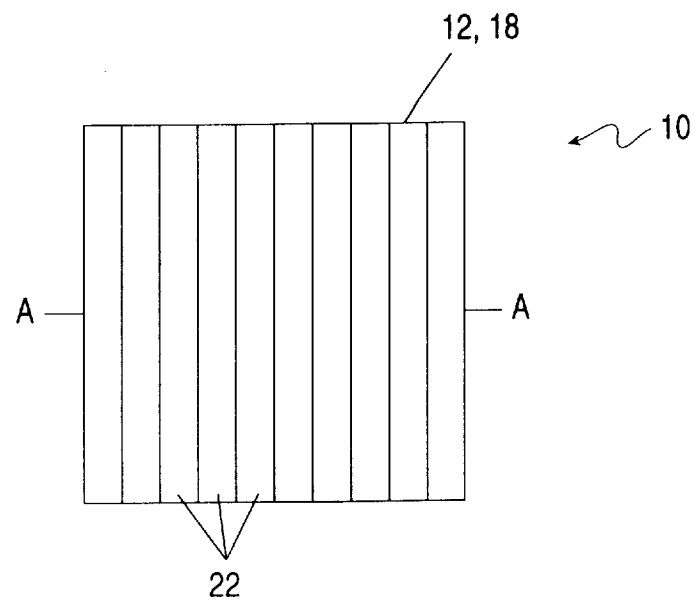
FIG. 1A shows the obverse side of a first basic device of the present invention.
Figure 1B:
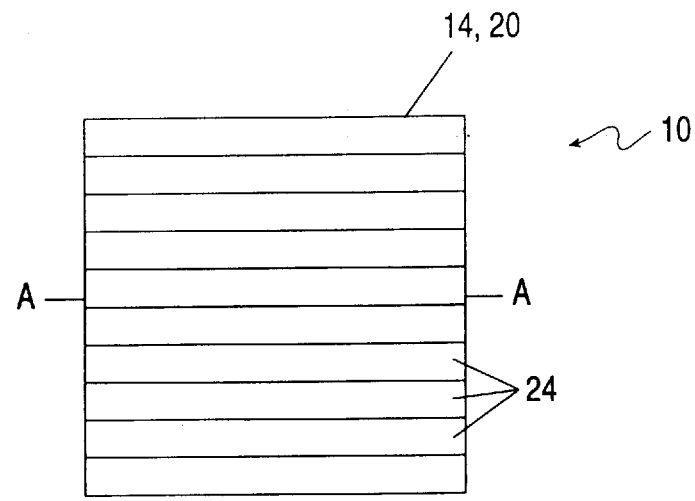
FIG. 1B shows the reverse side of the device of FIG. 1A.
Figure 1C:
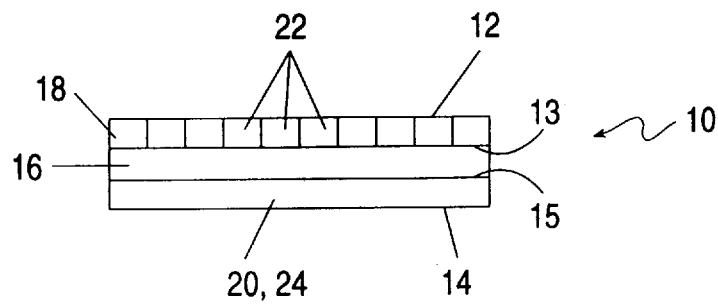
FIG. 1C is a lateral cross-section of the device of FIG. 1A.

Referring now to the drawings, FIG. 1A shows the obverse 12 side of a first basic device 10 of the present invention, for recording distributed subimages; FIG. 1B shows the reverse 14 side of device 10; and FIG. 1C shows a lateral cross-section of device 10 along cut A—A. The core of the present invention is a layer 16 of a storage phosphor material such as ZnSi:Cu, about 50 microns thick. Layer 16 is a rectangle that is geometrically similar to a standard CCD array, with parallel obverse 13 and reverse 15 faces. A typical size of layer 16 is 240 mm×180 mm. Layer 16 is sandwiched between two arrays 18 and 20 of linear electrodes 22 and 24. Array 18 is on obverse face 13, and array 20 is on reverse face 15. Electrodes 22 are disposed at an angle to electrodes 24. Although the scope of the present invention includes devices 10 in which electrodes 22 and 24 are disposed at any non-zero mutual angle, it is preferable that electrodes 22 and 24 be mutually perpendicular, as shown. Electrodes 22 are made of an electrically conducting material such as $SnO_2$ and are sufficiently thin to be substantially transparent to x-rays. Electrodes 24 are made of an electrically conducting material such as $SnO_2$ or indium-tin-oxide that is transparent to the phosphorescence emitted by storage phosphor layer 16. In each of arrays 18 and 20, electrodes 22 or 24 are separated by thin regions of insulating material, to isolate electrodes 22 or 24 electrically from each other. For illustrative purposes, 10 electrodes 22 and 10 electrodes 24 are shown. To achieve the objective of the present invention of obtaining high resolution images, it is preferable that there be at least 2000 electrodes 22 and at least 2000 electrodes 24.

Figure 2A:
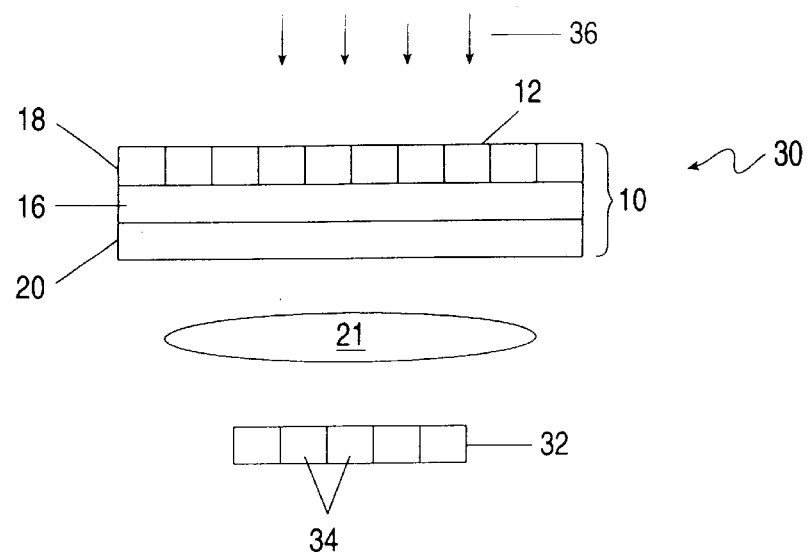
FIG. 2A is a lateral cross-section of a first preferred embodiment of the device of the present invention.
Figure 2B:
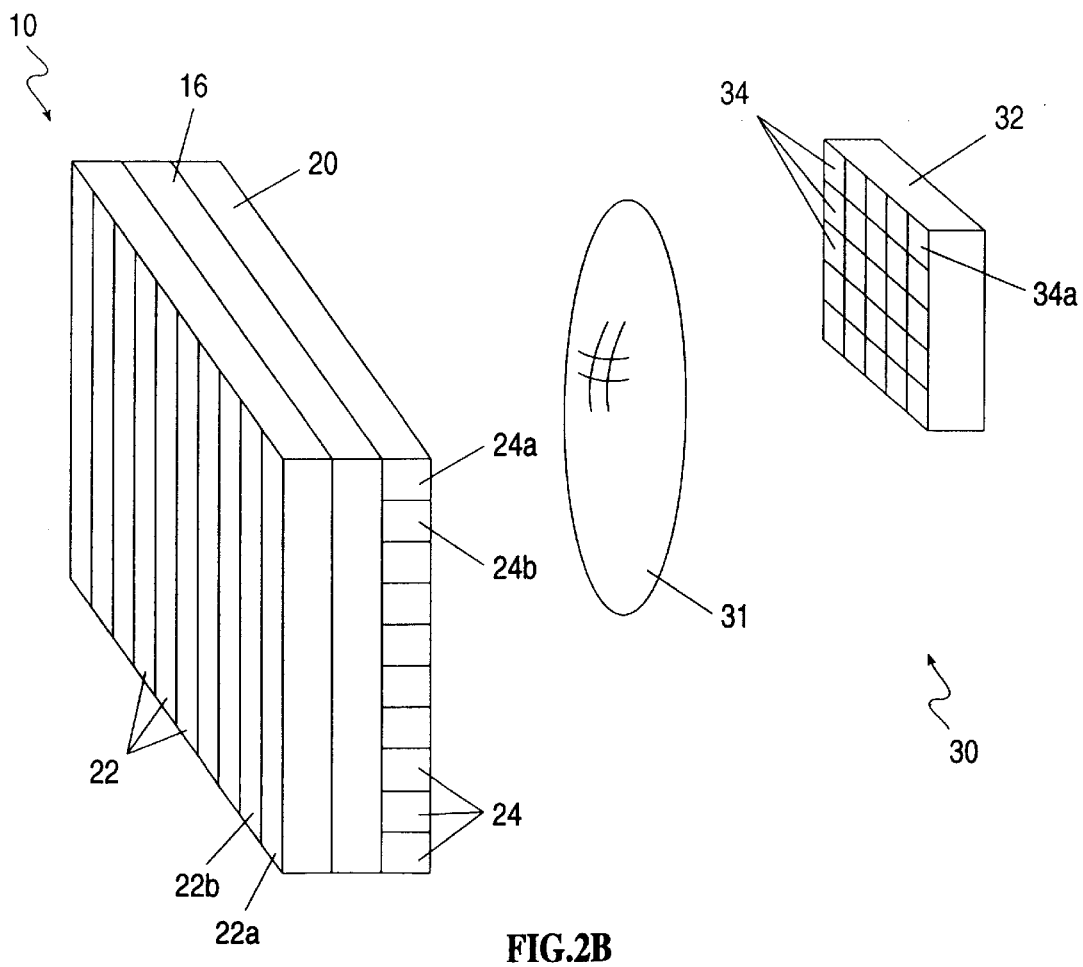
FIG. 2B is an exploded perspective view of the device of FIG. 2A.

FIGS. 2A and 2B illustrate a first preferred embodiment 30 of the device of the present invention. FIG. 2A is a schematic lateral cross-section of embodiment 30. FIG. 2B is a schematic perspective view of embodiment 30. Embodiment 30 includes, in addition to basic device 10, a CCD array 32 of 25 detector elements 34 and an optical imaging system, represented symbolically by a lens 31, that images light emerging from basic device 10 onto CCD array 32.

Optical imaging system 31 may be based on refractive and reflective elements such as lenses, mirrors and prisms, or may be based on optical waveguides. Each CCD detector element 34 corresponds to two electrodes 22 and two electrodes 24. In general, the ratio of the number of electrodes 22 in array 18 to the number of CCD detector elements 34 in each row of array 32 is an integer, as is the ratio of the number of electrodes 24 in array 20 to the number of CCD detector elements 34 in each column of array 32, so that each CCD detector element 34 corresponds to an integral number of electrodes 22 and an integral number of electrodes 24. Furthermore, no electrode 22 corresponds to more than one CCD detector element 34 of each row of array 32 and no electrode 24 corresponds to more than one CCD detector element 34 of each column of array 32. As noted above, the depiction of only 10 electrodes 22, 10 electrodes 24, and 5 CCD detector elements 34 in each row or column of array 32 is only illustrative. In a typical embodiment 30, there are 2000 electrodes 22 and 2000 electrodes 24, and array 32 is a 1000×1000 array of CCD detector elements 34.

CCD array 32 is connected in the conventional manner to a data collection and storage device (not shown). Electrode arrays 18 and 20 are similarly connected to a control device operative to address and activate sequentially four different subsets of electrodes 22 and 24: a first subset including odd-numbered electrodes 22 and odd-numbered electrodes 24; a second subset including odd-numbered electrodes 22 and even-numbered electrodes 24; a third subset including even-numbered electrodes 22 and odd-numbered electrodes 24; and a fourth subset including even-numbered electrodes 22 and even-numbered electrodes 24. When a subset is activated, all of its electrodes are activated simultaneously. Preferably, the data collection and storage device and the control device are based on the same microprocessor-controlled device such as a personal computer.

To use device 30, obverse side 12 of device 30 is exposed to x-rays 36 passing through an object (not shown) that is partly opaque to x-rays, thereby creating a latent image of the object in storage phosphor layer 16. To read the first subimage of the latent image, a voltage of between 80% and 90% of the threshold voltage of 50 to 60 volts DC is applied simultaneously to electrodes 22 of the first subset, and a voltage of the same magnitude but opposite polarity is applied simultaneously to electrodes 24 of the first subset. An electrode 22 or 24 to which such a voltage is applied is referred to herein as an "activated" electrode, and the process of applying the voltage to electrode 22 or 24 is referred to as "activating" electrode 22 or 24. When a particular electrode 22 and a particular electrode 24 are activated, the subportion of storage phosphor layer 16 where those two electrodes intersect is subjected to a voltage that exceeds the threshold voltage by between 60% and 80%, so that subportion of storage phosphor layer 16 emits phosphorescent light at an intensity proportional to the intensity of the latent x-ray image recorded in that portion of storage phosphor layer 16. This phosphorescent light is focused by optical imaging system 31 onto CCD array 32, with light from one subportion focused on one and only one corresponding CCD detector element 34. The corresponding subimage is stored by the data collection and storage device as the first subimage. With the first subimage now stored in the data collection and storage device, the second electrode subset is activated, again producing phosphorescent light that is focused by optical imaging system 31 onto CCD array 32, one subportion per CCD detector element 34, and the second subimage is stored. Then the third electrode subset is activated, and the third subimage is stored. Finally, the fourth electrode subset is activated and the fourth subimage is stored. Because four neighboring intersection regions, each from a different subset of electrodes, correspond to one CCD detector element 34, one CCD detector element 34 can be used sequentially to acquire four distinct pixels of the latent image. For example, the intersection region of electrode 22a, of the odd-numbered electrodes 22, and electrode 24a, of the odd numbered electrodes 24, the intersection region of electrode 22b, of the even-numbered electrodes 22, and electrode 24a, of the odd-numbered electrodes 22, and electrode 24b, of the even-numbered electrodes 22, and electrode 24b, of the even numbered electrodes 24, constitute a set of intersection regions, such that optical imaging system 31 directs light from all members of the set to the same CCD detector element 34a. After all four electrode subsets have been activated and all four subimages have been stored, the four subimages are interleaved to produce the final image.

Figure 3:
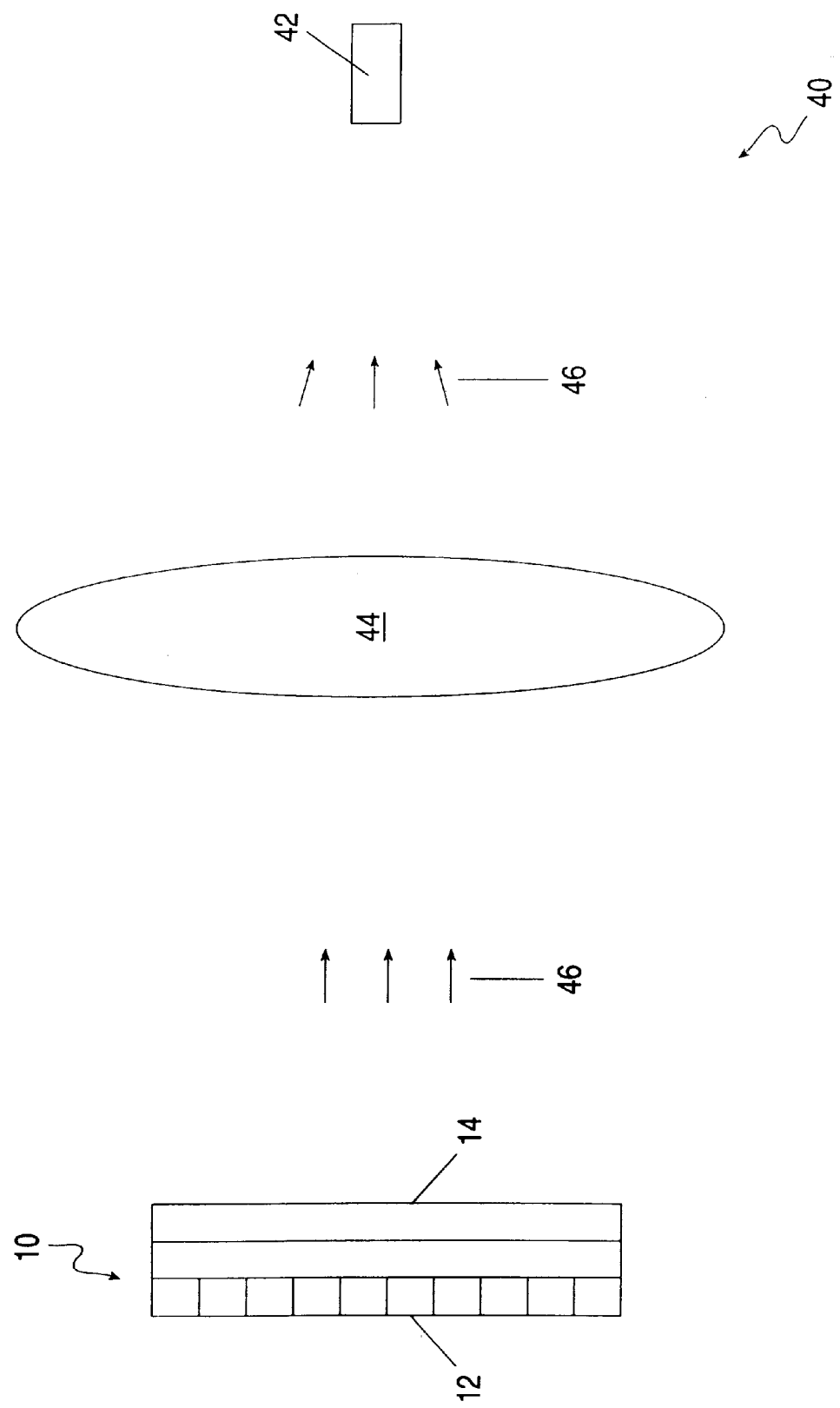
FIG. 3 is a partial schematic depiction of a second preferred embodiment of the device of the present invention.

FIG. 3 is a partial schematic depiction of a second preferred embodiment 40 of the device of the present invention. In embodiment 40, an optical imaging system, represented symbolically by a lens 44, focuses phosphorescent light 46 from basic device 10 onto a photomultiplier 42. In the use of embodiment 40, instead of activating subsets of electrodes 22 and 24, pairs of electrodes 22 and 24 are activated separately and sequentially. In this way, the pixels of the latent image are addressed sequentially.

Figure 4A:
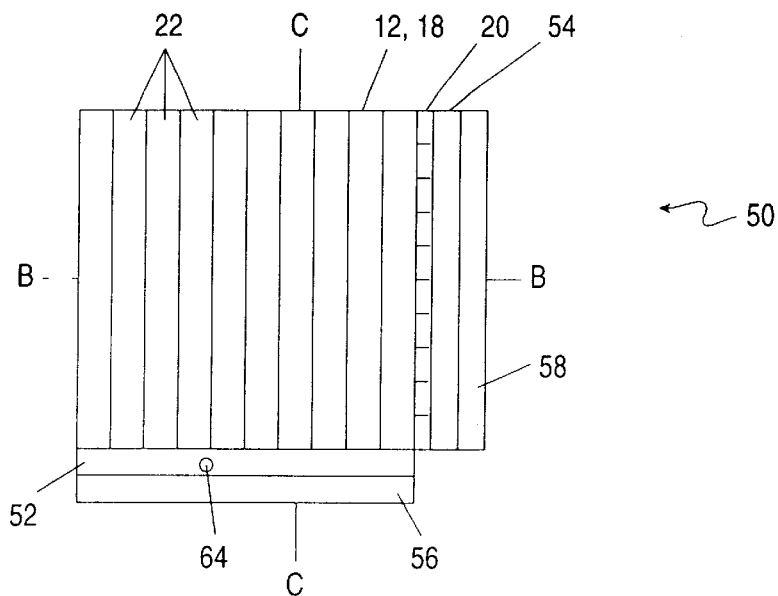
FIG. 4A shows the obverse side of a third preferred embodiment of the device of the present invention.
Figure 4B:
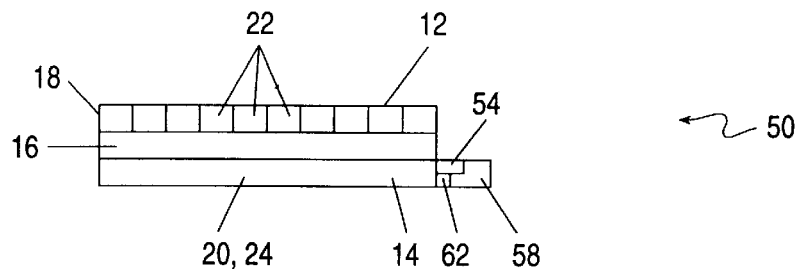
FIGS. 4B and 4C are cross-sections of the device of FIG. 4A.
Figure 4C:
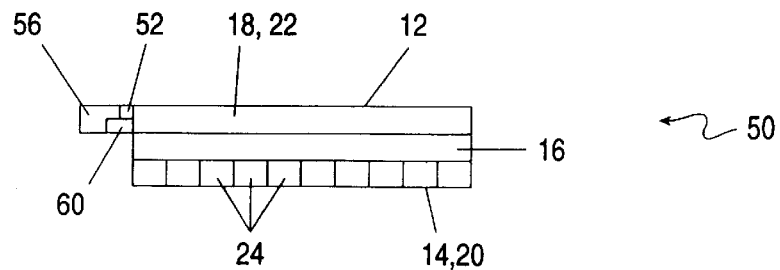

FIGS. 4A, 4B and 4C are partial depictions of a variant 50 of basic device 10, configured for simple, rapid addressing and activating of electrodes 22 and 24 in the context of preferred embodiment 40. FIG. 4A shows obverse side 12 of device 50. FIG. 4B is a cross-section of device 50 along cut B—B. FIG. 4C is a cross-section of device 50 along cut C—C. In addition to the components of basic device 10, device 50 includes two photoconductive strips 52 and 54. Strip 52 is adjacent and perpendicular to all electrodes 22, as shown. Similarly, strip 54 is adjacent and perpendicular to all electrodes 24. Strip 52 rests on an electrically conductive band 56 that also spans all electrodes 22. Band 56 is isolated from electrodes 22 by an electrically insulating region 60. Similarly, strip 54 rests on an electrically conductive band 58 that also spans all electrodes 24 and that is isolated from electrodes 24 by an electrically insulating region 62. Note that electrode array 20 protrudes slightly to the right of electrode array 18 and storage phosphor layer 16 in FIG. 4A. Conductive bands 56 and 58 are connected to a DC power source (not shown) that keeps the voltage difference between bands 56 and 58 at between 160% and 180% of the threshold voltage of storage phosphor layer 16.

To establish electrical contact between one of electrodes 22 and conductive band 56, thereby activating only that electrode 22, photoconductive strip 52 is illuminated locally, adjacent to the target electrode 22, with a spot 64 of light. Light spot 64 reversibly converts the illuminated portion of photoconductive strip 52 from an electrical insulator to an electrical conductor.

Figure 5:
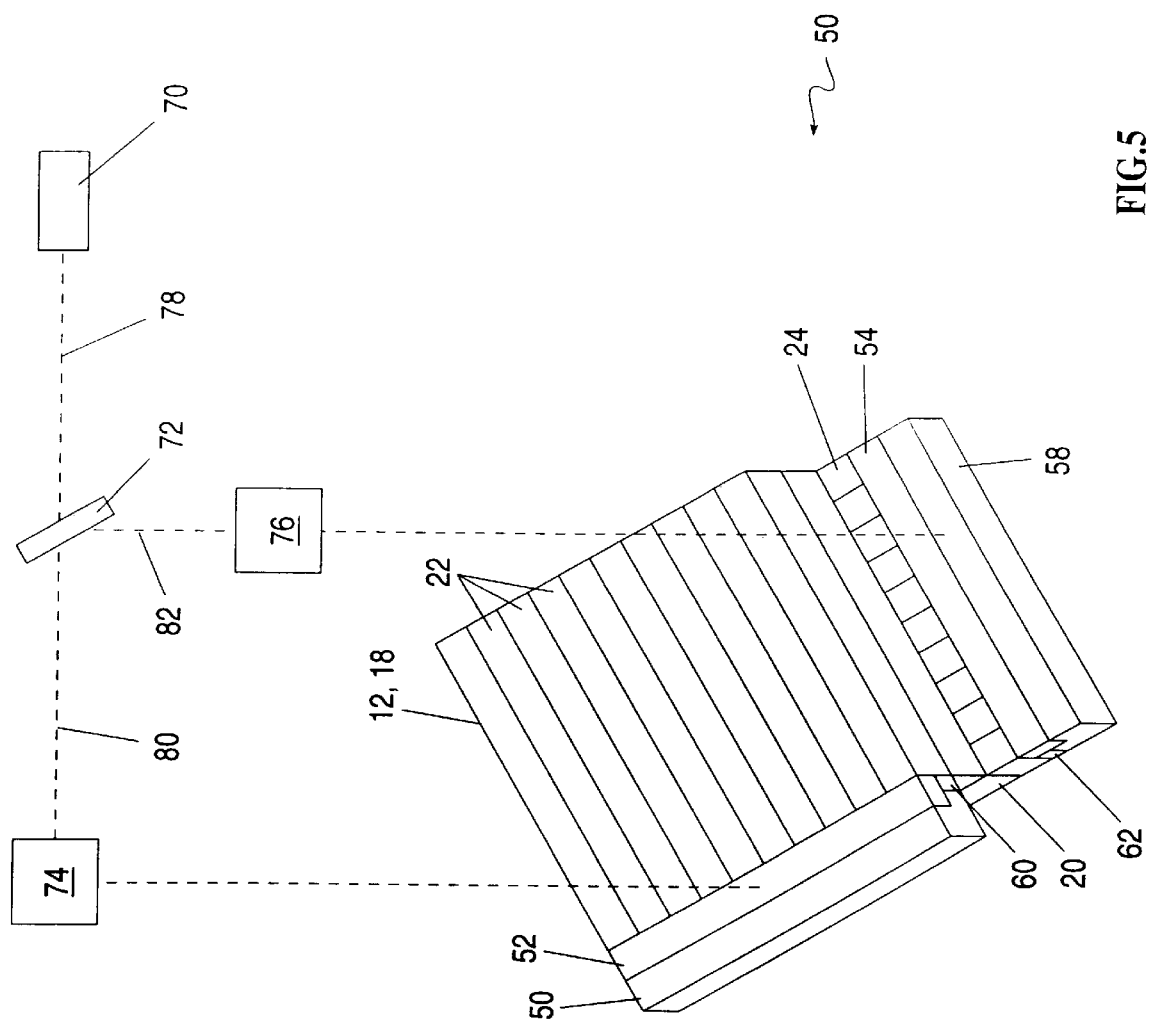
FIG. 5 is a schematic depiction of the reading of the latent image from the device of FIG. 4A.

FIG. 5 is a schematic depiction, partly in perspective, of how a latent x-ray image is read from device 50. A source 70, such as a laser, of a collimated beam 78 of light is directed at a beamsplitter 72, which splits beam 78 into two sub-beams 80 and 82. Sub-beam 80 is directed by a scanning mechanism 74 at photoconductive strip 52. Sub-beam 82 is directed by a scanning mechanism 76 at photoconductive strip 54. Scanning mechanisms 74 and 76 include movable reflectors such as prisms or mirrors for aiming sub-beams 80 and 82 at spots such as spot 64 that are adjacent to one and only one of electrodes 22 or 24. The construction and operation of scanning mechanisms 74 and 76 are well-known in the art and therefore are not elaborated herein. The cross-section of beam 78, and hence of sub-beams 80 and 82, is smaller than the widths of electrodes 22 and 24, so that electrical contact is established only between conductive bands 56 and 58 and the single electrodes 22 and 24 to be activated.

It will be appreciated that many other similar optical schemes may be used for selectively activating electrodes 22 and 24. For example, several light sources may be used, or several beamsplitters may be used to split beam 78 into several sub-beams, thereby enabling the simultaneous activation of electrodes 22 and 24 in subsets, as described above.

As electrodes 22 and 24 are sequentially activated, in pairs or in subsets, for example by light beam 78, the phosphorescence stimulated between each pair of activated electrodes is detected by light-detection mechanisms such as CCD array 32 or the photomultiplier-based system of FIG. 3. Alternatively, if the electrodes are activated pairwise, the fact that stimulating phosphorescent emission from a portion of storage phosphor 16 also increases the electrical conductivity of that region, by an amount proportional to the intensity of the latent image pixel stored in that region, is exploited to provide a direct electronic readout of the latent image pixel. Specifically, the current, that flows in the circuit created when each electrode pair is activated, is measured to give a direct indication of the electrical conductivity of the stimulated portion of storage phosphor 16.

Figure 6:
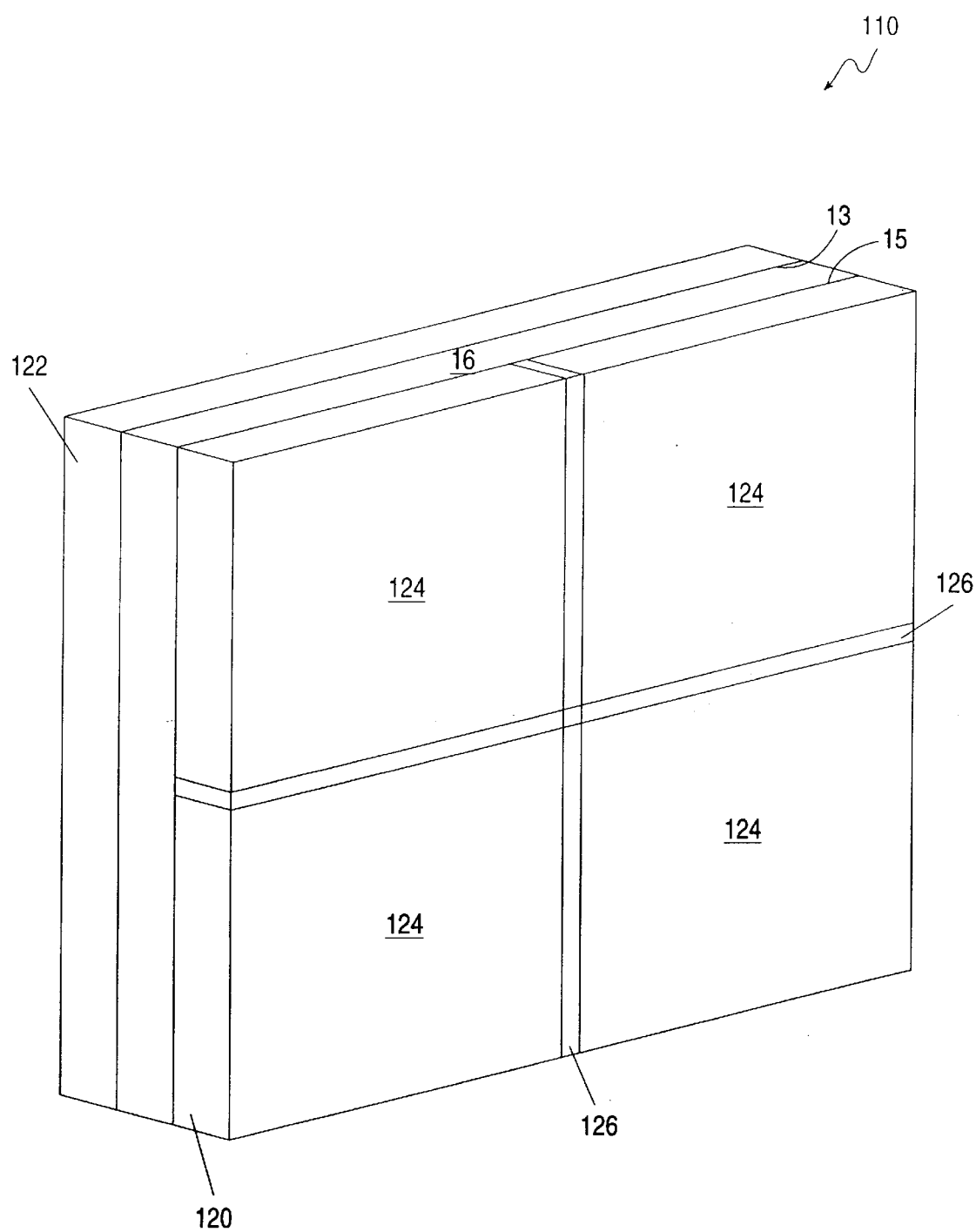
FIG. 6 is a perspective view of a second basic device of the present invention.

FIG. 6 shows, in perspective, a second basic device 110 of the present invention, for recording contiguous subimages. In device 110, storage phosphor layer 16 is sandwiched between a single electrode 122 on obverse face 13 and an array 120 of rectangular electrodes 124 on reverse face 15. As in device 10, electrode 122 is made of an electrically conducting material that is transparent to x-rays, and electrodes 124 are made of an electrically conducting material that is transparent to the phosphorescence emitted by storage phosphor layer 16. Each electrode 124 defines between itself and electrode 122 a contiguous portion of storage phosphor layer 16 that is stimulated to emit phosphorescent light when that electrode 124 and electrode 122 are activated. Electrodes 124 are separated by thin strips 126 of an insulating material. For illustrative purposes, only four electrodes 124 are shown. In typical practice, up to 12 electrodes 124 are used.

Figure 7:
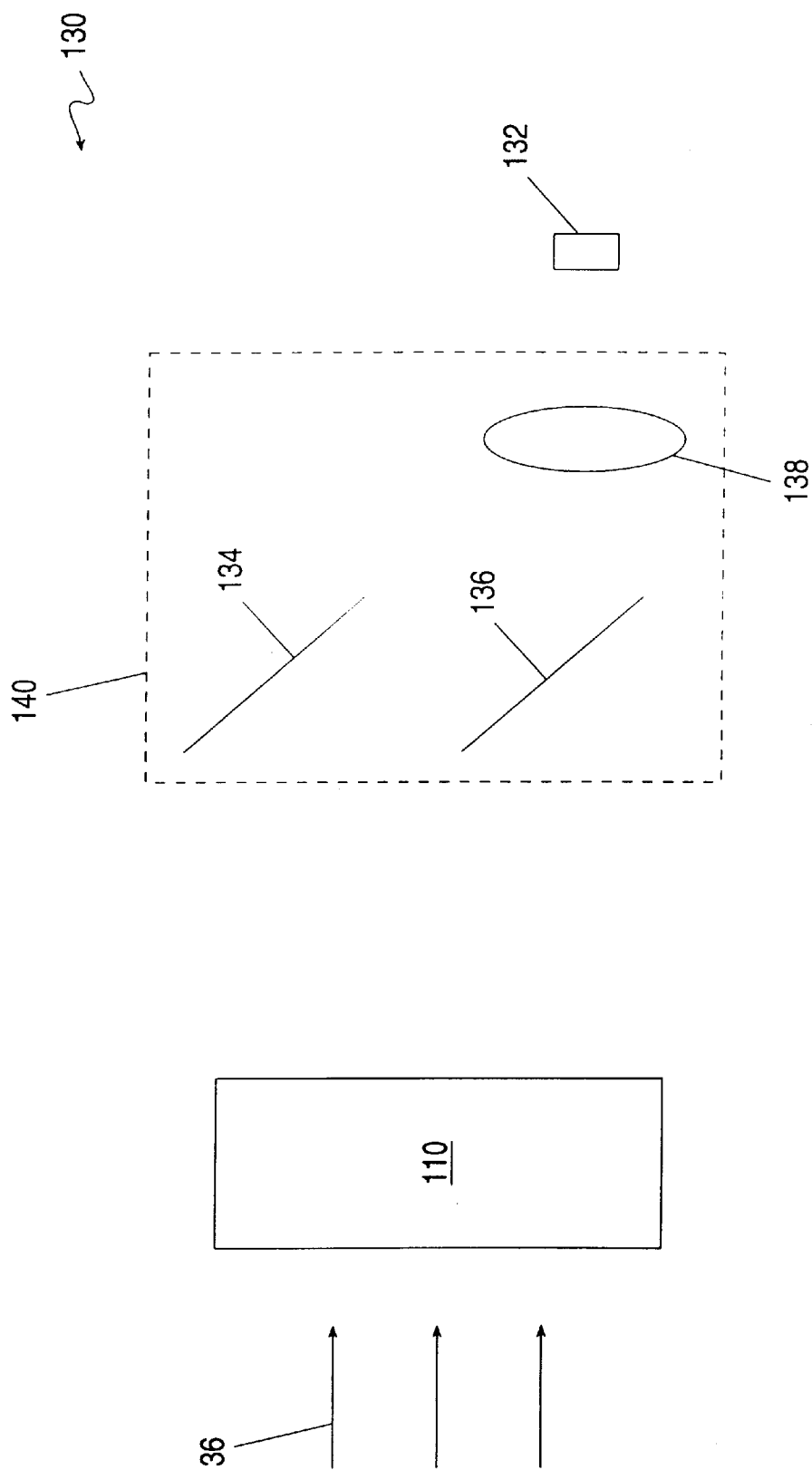
FIG. 7 is a schematic side view of a preferred embodiment of the device of the present invention based on the device of FIG. 6.

FIG. 7 is a schematic side view of an embodiment 130 of a device of the present invention based on basic device 110. An optical system 140 is provided that focuses light, emitted from each of the four portions of storage phosphor layer 16 between electrode 122 and electrodes 124, onto a CCD array 132. Optical system 140 includes a focusing mechanism, represented symbolically by a lens 148, for focusing light onto CCD array 132, and a periscopic mechanism, represented symbolically by a reflector 134 and a beamsplitter 136, for directing light from the four portions of storage phosphor layer 16 between electrode 122 and electrodes 124 to focusing mechanism 138. It will be obvious to one ordinarily skilled in the art how to assemble a group of optical components, such as prisms, mirrors, beamsplitters and symmetric or asymmetric lenses, to achieve the ends of optical system 140.

CCD array 132 is connected in the conventional manner to a data collection and storage device (not shown). Electrodes 122 and 124 are similarly connected to a control device operative to activate electrodes 122 and 124. As in the case of device 30, the data collection and storage device and the control device preferably are based on the same microprocessor-controlled device such as a personal computer. To use device 130, the side of device 110 bearing electrode 122 is exposed to x-rays 36 passing through an object (not shown) that is partly opaque to x-rays, thereby creating a latent image of the object in storage phosphor layer 16. To read the latent image, each electrode 124 is activated sequentially along with electrode 122, causing the emission of phosphorescent light from the portion of storage phosphor layer 16 between that electrode 124 and electrode 122. This phosphorescent light is focused by imaging system 140 onto CCD array 132. The data collection and storage device reads CCD array 132 and stores the corresponding subimage, which has the resolution of CCD array 132, i.e., as many pixels as there are CCD detector elements in CCD array 132. After all electrodes 124 have been separately activated and all corresponding subimages have been stored, the subimages are mosaiced to form the final high-resolution image.

While the invention has been described with respect to a limited number of embodiments, it will be appreciated that many variations, modifications and other applications of the invention may be made.

What is claimed is:

1. An imaging system comprising:
   (a) a storage phosphor layer having two parallel planar faces;
   (b) a first plurality of parallel linear electrodes on a first of said two faces of said storage phosphor layer; and
   (c) a second plurality of parallel linear electrodes on a second of said two faces of said storage phosphor layer, said electrodes of said second plurality being oriented at an angle to said electrodes of said first plurality.

2. The imaging system of claim 1, wherein said electrodes of said first plurality are made of a material substantially transparent to x-rays.

3. The imaging system of claim 1, wherein said electrodes of said second plurality are made of a material transparent to visible light.

4. The imaging system of claim 1, wherein said electrodes of said first plurality and said electrodes of said second plurality are substantially mutually perpendicular.

5. The imaging system of claim 1, further comprising:
   (d) a mechanism for detecting light emitted from said storage phosphor layer.

6. The imaging system of claim 5, wherein said mechanism includes a CCD array.

7. The imaging system of claim 6, wherein said first and second pluralities of electrodes define between them a plurality of intersections grouped into a plurality of groups of neighboring said intersections, the imaging system further comprising:
   (e) an optical imaging system operative to direct light from each of said groups to one and only of said detectors.

8. The imaging system of claim 5, wherein said mechanism includes a photomultiplier.

9. The imaging system of claim 1, further comprising:
   (d) a first photoconductive strip adjacent to said electrodes of said first plurality; and
   (e) a second photoconductive strip adjacent to said electrodes of said second plurality.

10. The imaging system of claim 9, further comprising:
    (f) a mechanism for simultaneously illuminating a portion of said first photoconductive strip adjacent to one of said electrodes of said first plurality and a portion of said second photoconductive strip adjacent to one of said electrodes of said second plurality.

11. The imaging system of claim 9, wherein said illumination mechanism includes:
  (i) a source of a collimated beam of light, and
  (ii) a mechanism for directing said collimated beam of light simultaneously at said portion of said first photoconductive strip and at said portion of said second photoconductive strip.

12. A method for acquiring a high-resolution x-ray image, comprising the steps of:
  (a) providing an imaging system including:
    (i) a storage phosphor layer having two parallel planar faces,
    (ii) a first plurality of parallel linear electrodes on a first of said two faces of said storage phosphor layer, and
    (iii) a second plurality of parallel linear electrodes on a second of said two faces of said storage phosphor layer, said electrodes of said second plurality being oriented at an angle to said electrodes of said first plurality;
  (b) exposing said storage phosphor layer to the x-rays, thereby creating a latent image in said storage phosphor layer; and
  (c) for each electrode of said first plurality and each electrode of said second plurality: applying a voltage difference, between said each electrode of said first plurality and said each electrode of said second plurality, sufficient to stimulate emission of light from a portion of said storage phosphor layer between said each electrode of said first plurality and said each electrode of said second plurality.

13. The method of claim 12, further comprising the step of:
  (d) recording said light emitted from said portions of said storage phosphor layer.

14. The method of claim 13, wherein said recording is effected using a CCD array.

15. The method of claim 14, wherein said voltage difference is applied simultaneously to at least a portion of said electrodes of said first plurality and at least a portion of said electrodes of said second plurality, so that, for each electrode of at least said portion of said electrodes of said first plurality and for each electrode of at least said portion of said electrodes of said second plurality, said light emitted, from said portion of said storage phosphor layer between said each electrode of at least said portion of said first plurality of electrodes and said each electrode of at least said portion of said second plurality, impinges on one and only one of said detectors.

16. The method of claim 13, wherein said recording is effected using a photomultiplier.

17. The method of claim 16, wherein said voltage difference is applied successively to said each electrode of said first plurality and said each electrode of said second plurality.

18. The method of claim 12, further comprising the step of:
  (d) for each electrode of said first plurality and each electrode of said second plurality: measuring a current flow between said each electrode of said first plurality and said each electrode of said second plurality concurrently with said applying of said voltage difference between said each electrode of said first plurality and said each electrode of said second plurality.

19. The method of claim 12, wherein said imaging system further includes:
  (iv) a first photoconductive strip adjacent to said electrodes of said first plurality, and
  (v) a second photoconductive strip adjacent to said electrodes of said second plurality;
and wherein said applying of said voltage difference between said each electrode of said first plurality and said each electrode of said second plurality is effected by steps including simultaneously illuminating a region of said first photoconductive strip adjacent to said each electrode of said first plurality and a region of said second photoconductive strip adjacent to said each electrode of said second plurality.

20. An imaging system comprising:
  (a) a storage phosphor layer having two parallel planar faces;
  (b) a stimulation mechanism operative to stimulate emission of light from only a portion of said storage phosphor layer, wherein said portion of said phosphor area is contiguous, and wherein said stimulation mechanism includes:
    (i) a first electrode on a first of said of said two faces of said storage phosphor layer;
    (ii) a plurality of second electrodes on a second of said two faces of said storage phosphor layer, opposite said first electrode;
  said contiguous portion of said storage phosphor layer being between said first electrode and said second electrode, said first electrode and each of said second electrodes defining between them a different contiguous portion of said storage phosphor layer; and
  (c) an imaging mechanism operative to detect all of said light substantially simultaneously as an image including a plurality of pixels.

21. An imaging system, comprising:
  (a) a storage phosphor layer;
  (b) a stimulation mechanism operative to stimulate emission of light from only a portion of said storage phosphor layer; wherein said portion of said storage phosphor layer includes a plurality of distributed subportions; and
  (c) an imaging mechanism operative to detect all of said light substantially simultaneously as an image including a plurality of pixels.

22. The imaging system of claim 21, wherein said storage phosphor layer has two parallel faces, and wherein said stimulation mechanism includes:
  (i) a first plurality of parallel linear electrodes on a first of said two faces of said storage phosphor layer; and
  (ii) a second plurality of parallel linear electrodes on a second of said two faces of said storage phosphor layer, said electrodes of said second plurality being oriented at an angle to said electrodes of said first plurality;
each of said subportions of said storage phosphor layer being between one of said first electrodes and one of said second electrodes.

23. The imaging system of claim 22, wherein each of said pixels corresponds to one of said subportions.

24. The imaging system of claim 22, wherein said stimulation mechanism includes at least two of said first pluralities of said parallel linear electrodes on said first face of said storage phosphor layer, each of said at least two first pluralities and said second plurality defining between them a different portion of said storage phosphor layer.

25. The imaging system of claim 24, wherein said at least two first pluralities of said parallel linear electrodes are interleaved on said first face of said storage phosphor layer.

26. The imaging system of claim 22, wherein said electrodes of said first plurality and said electrodes of said second plurality are substantially mutually perpendicular.

27. An imaging system comprising:
(a) a storage phosphor layer;
(b) a stimulation mechanism operative to stimulate emission of light from only a portion of said storage phosphor layer; and
(c) an imaging mechanism operative to detect all of said light substantially simultaneously as an image including a plurality of pixels; wherein said imaging mechanism includes an array of detector elements, each of said elements corresponding to one of said pixels.

28. A method for acquiring a high-resolution x-ray image, comprising the steps of:
(a) providing a storage phosphor layer;
(b) exposing said storage phosphor layer to the x-rays, thereby creating a latent image in said storage phosphor layer;
(c) stimulating emission of light from only a portion of said storage phosphor layer; and
(d) imaging said emitted light substantially as a plurality of pixels, thereby creating a subimage of said latent image
wherein said steps of stimulating and imaging are effected sequentially for a plurality of said portions of said storage phosphor layer, thereby creating a plurality of said subimages of said latent images.

29. The method of claim 28, wherein said imaging is effected using an array of detector elements, each of said detector elements corresponding to one and only one of said pixels of each of said subimages.

30. The method of claim 28, further comprising the step of:
(e) assembling said subimages to create a final image.

31. The method of claim 30, wherein each of said portions is contiguous, and wherein said assembling is effected by mosaicing said subimages.

32. The method of claim 30, wherein each of said portions includes a plurality of distributed subportions, and wherein said assembling is effected by interleaving said subimages.

33. A method for acquiring a high-resolution x-ray image, comprising the steps of:
(a) providing a storage phosphor layer;
(b) exposing said storage phosphor layer to the x-rays, thereby creating a latent image in said storage phosphor layer;
(c) stimulating emission of light from only a portion of said storage phosphor layer; and
(d) imaging said emitted light substantially simultaneously as a plurality of pixels, thereby creating a subimage of said latent image;
wherein said imaging is effected using an array of detector elements, each of said detectors corresponding to one and only one of said pixels.

* * * * *